US005840548A

United States Patent [19]
Ogihara et al.

[11] Patent Number: 5,840,548
[45] Date of Patent: Nov. 24, 1998

[54] PROCESS FOR PRODUCING MICROBIAL LIPIDS FROM HYDROCARBONS

[75] Inventors: Kimihiko Ogihara; Masamichi Sato; Kazunori Ishigami; Kouki Sakashita; Yoshihiro Takayama, all of Tokyo, Japan

[73] Assignee: Kashima Oil Co., Ltd., Tokyo, Japan

[21] Appl. No.: 527,335

[22] Filed: Sep. 12, 1995

[30] Foreign Application Priority Data

Sep. 13, 1994 [JP] Japan ................................ 6-219205
Dec. 12, 1994 [JP] Japan ................................ 6-307998

[51] Int. Cl.$^6$ ............................ C12P 7/64; C12P 7/62
[52] U.S. Cl. ........................ 435/134; 435/135; 435/244
[58] Field of Search ............................ 435/134, 135, 435/170, 244

[56] References Cited

FOREIGN PATENT DOCUMENTS

| 230 561 | 12/1985 | Germany . |
| 255 052 | 3/1988 | Germany . |
| 2-249491 | 10/1991 | Japan . |
| 3-280888 | 12/1991 | Japan . |
| 6-253866 | 9/1994 | Japan . |
| 6-253867 | 9/1994 | Japan . |
| 6-253868 | 9/1994 | Japan . |

OTHER PUBLICATIONS

Tahara et al., Agr. Biol. Chem., 40(7), 1449–1450, 1976.
Gerson et al., Appl. Microbiol., 1975, vol. 30., pp. 193–198, 1975.
Cooper et al., J. Ferment. Technol., vol. 60, pp. 19–24. 1982.
Hallas et al., Can J. Microbiol., vol. 24, pp. 1197–1203, 1987.
Martin et al., Carbohydr. Res., vol. 220, pp. 93–100, 1991.
Ascenzi et al., J. Bacteriol., vol. 137, pp. 384–390, 1979.
Kim et al., J. of Biotechnol., vol. 13, pp. 257–266, 1990.
Schulz et al., Z. Naturforsch., 46c, 197–203, 1991.
Passeri et al., Z. Naturforsch., 46, 204–209, 1991.
Goodfellow et al., "The Biology of the Actinomycetes", 1984, pp. 77–79, Academic Press.
Chemical Abstracts, vol. 108, No. 5, p. 338, AN 34 628Z, Feb. 1, 1988.
Chemical Abstracts, vol. 73, No. 23, pp, 256–257, AN 119 149C, Dec. 7, 1970.
Chemical Abstracts, vol. 70, No. 11, p. 104, AN 45 065M, Mar. 17, 1969.
Patent Abstracts of Japan, vol. 6, No. 250 (C–139) [1128], Dec. 9, 1982, JP–A–57 145 896, Sep. 9, 1982.

*Primary Examiner*—Irene Marx
*Attorney, Agent, or Firm*—Oblon, Spivak, McClelland, Maier & Neustadt, P.C.

[57] ABSTRACT

The present invention relates to a process for producing lipids, which comprises culturing bacteria capable of assimilating aliphatic hydrocarbons and accumulating lipids in medium containing aliphatic hydrocarbons until lipids are accumulated in the bacteria and then recovering the lipids therefrom, as well as to process for producing cosmetics which comprises using the lipids produced by said method.

14 Claims, No Drawings

PROCESS FOR PRODUCING MICROBIAL LIPIDS FROM HYDROCARBONS

BACKGROUND OF THE INVENTION

1. Field of the Invention

The present invention relates to a process for producing lipids from aliphatic hydrocarbons by means of bacteria, as well as the use, as cosmetics, of lipids produced by said process. The lipids obtained according to the present invention are widely used as raw materials etc. for surface active agents, food additives, and fatty acids in a wide variety of fields such as oil chemistry, petroleum chemistry, pharmaceuticals, agricultural chemicals, cosmetics and foods.

2. Description of the Prior Art

Conventionally, lipids have been produced from plant and animal sources such as beef tallow, palm oil, etc., but these naturally occurring materials are disadvantageous in that their supply and price greatly vary depending on the weather and other factors. The production of lipids from petroleum and/or petroleum chemicals via organic synthesis is also known but is still not industrially practiced.

In recent years, γ-linolenic acid-containing lipids as substitutes for evening-primrose oil are industrially produced using the functions of mold, but in this process, too, naturally occurring sugars such as glucose etc. are used as the carbon source.

OBJECTS AND SUMMARY OF THE INVENTION

As a result of their eager research, the present inventors found that lipids are accumulated in bacteria capable of assimilating aliphatic hydrocarbons and accumulating lipids by culture thereof in medium containing aliphatic hydrocarbons.

The process for producing lipids according to the present invention comprises culturing bacteria capable of assimilating aliphatic hydrocarbons and accumulating lipids in medium containing aliphatic hydrocarbons until lipids are accumulated in the bacteria and then recovering the lipids therefrom.

The bacteria used in the present invention may be any of those capable of assimilating aliphatic hydrocarbons and accumulating lipids, including but not limited to those belonging to the genera Mycobacterium, Agrobacterium, Rhizobium, Corynebacterium, Rhodococcus, Arthrobacter and Brevibacterium, more specifically *Mycobacterium sp.* KO-201 (FERM BP-5157), *Agrobacterium sp.* KO-202 (FERM BP-5158), *Rhizobium sp.* KO-203 (FERM BP-5159), *Corynebacterium fujiokense* ATCC 21496, *Rhodococcus rhodochrous* ATCC 13808, *Arthrobacter paraffineus* ATCC 15591 and *Brevibacterium ketoglutamicum* ATCC 15588.

Out of the bacteria enumerated above, *Mycobacterium sp.* KO-201 was isolated from soil for the first time by the present inventors, and its bacterial properties are as follows:

| | |
|---|---|
| shape | polymorphic bacillus |
| Gram stainability | positive |
| formation of spores | absent |
| motility | absent |
| acid fastness | positive |
| oxidase | negative |
| catalase | positive |
| arylsulfatase | positive |
| fragmentation | present |
| formation of aerial hypha | absent |
| diamino acid in cell wall | meso-diaminopimelic acid |
| glycolyl test | glycolyl type |
| formation of mycolic acid | present |
| primary quinone system | MK-9(H$_2$) |

This strain was identified as a bacterium belonging to the genus Mycobacterium according to Bergey's Manual of Systematic Bacteriology etc. on the basis of its bacterial properties i.e. Gram-positive, polymorphic bacillus, acid fastness, non-motile, non spores, the presence of meso-diaminopimelic acid as the diamino acid in the cell wall, formation of mycolic acid, and arylsulfatase-positive. Further analysis indicated that this strain resembles *Mycobacterium chelonae* subsp. *chelonae,* but there are differences in the iron uptake, the degradation of sodium p-aminosalicylate and the ability to assimilate mannitol as shown in Table 1, so this strain was identified as a new bacterial species and designated *Mycobacterium sp.* KO-201. This strain, *Mycobacterium sp.* KO-201, has been deposited as FERM BP-5157 with the National Institute of Bioscience and Human-Technology, Agency of Industrial Science and Technology, 1-3, Higashi 1-chome-Tsukuba-shi, Ibaraki-ken, 305 Japan, on Jul. 6, 1995.

TABLE 1

| test items | *Mycobacterium* sp. KO-201 | *M. chelonae* subsp. chelonae |
|---|---|---|
| growth in the presence of 5% NaCl | − | − |
| growth in the presence of 0.2% picric acid | − | d |
| iron uptake | + | − |
| acid phosphatase | + | + |
| reduction of nitrate | − | d |
| growth in the presence of hydroxylamine hydrochloride (500 μg/ml) | + | + |
| growth in MacConkey's agar medium | + | + |
| growth in the presence of 0.01% Malachite Green | + | + |
| color of colonies | − | − |
| growth at 45° C. | − | − |
| degradation of p-aminosalicylate | − | + |
| formation of acids from sugars | | |
| L-arabinose | − | − |
| xylose | − | − |
| dulcitol | − | − |
| ability to assimilate | | |
| oxalate | − | − |
| citrate | + | + |
| mannitol | + | − |

*Agrobacterium sp.* KO-202 and *Rhizobium sp.* KO-203 were also isolated from soil for the first time by the present inventors, and their properties are as follows:

*Agrobacterium* sp. KO-202

| | |
|---|---|
| shape | bacillus |
| Gram stainability | negative |
| formation of spores | absent |
| motility | present |
| flagellar arrangement | peritrichous |

-continued

| | |
|---|---|
| attitude toward oxygen | aerobic |
| oxidase | positive |
| catalase | positive |
| OF test | oxidative |
| formation of 3-ketolactose | present |
| primary quinone system | Q-10 |
| *Rhizobium* sp. KO-203 | |
| shape | bacillus |
| Gram stainability | negative |
| formation of spores | absent |
| motility | present |
| flagellar arrangement | peritrichous |
| attitude toward oxygen | aerobic |
| oxidase | positive |
| catalase | positive |
| OF test | oxidative |
| formation of 3-ketolactose | absent |
| primary quinone system | Q-10 |

*Agrobacterium sp.* KO-202 was identified as a bacterium belonging to the genus Agrobacterium according to Bergey's Manual of Systematic Bacteriology etc. on the basis of its bacterial properties i.e. Gram-negative bacillus, motile by peritrichous flagella, aerobic, oxidase-positive, catalase-positive, oxidative degradation of sugars, formation of 3-ketolactose, and Q-10 as the primary quinone system.

*Rhizobium sp.* KO-203 was identified as a bacterium belonging to the genus Rhizobium according to Bergey's Manual of Systematic Bacteriology etc. on the basis of its bacterial properties i.e. Gram-negative bacillus, motile by peritrichous flagella, aerobic, oxidase-positive, catalase-positive, oxidative degradation of sugars, no 3-ketolactose formation, and Q-10 as the primary quinone system.

The present inventors found the accumulation of lipids in *Agrobacterium sp.* KO-202 and *Rhizobium sp.* KO-203, but there is no report of such significant accumulation of lipids in cells of the genus Agrobacterium or Rhizobium, so that these strains were considered new strains and designated *Agrobacterium sp.* KO-202 and *Rhizobium sp.* KO-203, respectively. These strains, *Agrobacterium sp.* KO-202 and *Rhizobium sp.* KO-203, have been deposited as FERM BP-5158 and FERM BP-5159 respectively with the National Institute of Bioscience and Human-Technology, Agency of Industrial Science and Technology, 1-3, Higashi 1-chome-Tsukuba-shi, Ibaraki-ken, 305 Japan, on Jul. 6, 1995.

The bacteria used in the present invention include mutants which were derived from the above bacteria by irradiation with ultraviolet rays or treatment with a mutagen such as N-methyl-N'-nitrosoguanidine etc.

The aliphatic hydrocarbons used in the present invention may be either of even-numbered or odd-numbered carbons, saturated or unsaturated, and straight chain or branched chain. The aliphatic hydrocarbons used in the present invention include, for example, pentane, hexane, heptane, octane, nonane, decane, undecane, dodecane, tridecane, tetradecane, pentadecane, hexadecane, heptadecane, octadecane, nonadecane, eicosane, heneicosane, docosane, tricosane, tetracosane, pentacosane, hexacosane, heptacosane, octacosane, nonacosane, triacontane, dimethylnonane, ethylnonane and methyltetradecane. Conventionally, use is made of aliphatic hydrocarbons with 5 to 30 carbon atoms, preferably 8 to 20 carbon atoms, which may be produced via chemical synthesis and/or fractional distillation of petroleum. These hydrocarbons are used singly or in combination depending on the object of lipids produced.

The lipids produced according to the present invention contain triglyceride as the main component in addition to diglyceride, monoglyceride, phospholipids, etc. If aliphatic hydrocarbons which contain a aliphatic hydrocarbons with odd-numbered carbons are used, the resulting lipids will contain fatty acid residues with odd-numbered carbons.

In the present invention, the above bacteria are cultured in medium containing aliphatic hydrocarbons to accumulate lipids in the bacteria and then the lipids are recovered.

The bacteria may be cultured under aerobic conditions after inoculated onto medium containing the above aliphatic hydrocarbons as the carbon source and if necessary sugars such as glucose, fructose, sucrose, etc., starch, nitrogen sources, inorganic salts, vitamins, optionally other nutrient sources. The nitrogen sources used in the medium include, for example, inorganic nitrogen sources such as ammonium sulfate, ammonium nitrate, ammonium chloride and ammonium phosphate, as well as organic nitrogen sources such as urea, yeast extract, peptone, glutamic acid, sodium glutamate, corn steep liquor and casamino acids. The inorganic salts include, for example, dipotassium hydrogen phosphate, potassium dihydrogen phosphate, sodium chloride, magnesium sulfate.$7H_2O$, zinc sulfate.$7H_2O$, $MnSO_4.nH_2O$, calcium chloride and iron (II) sulfate.$7H_2O$. If necessary, trace elements, vitamins, and other nutrient sources may also be used. The carbon source and other ingredients may be added at once prior to culture or by portions during culture. The medium pH is usually in the range of 4 to 8, preferably 4.5 to 7.5, and the temperature is usually in the range of 20° to 35° C., preferably 25° to 32° C. The culture conditions can be suitably determined depending on such factors as bacterial growth, the object of lipids produced, etc. Usually, the bacteria are cultured for 2 to 14 days under aerobic conditions in batch culture, half batch culture or continuous culture.

The method of recovering the lipids thus accumulated is not particularly limited insofar as the lipids can be efficiently recovered, and extraction with organic solvent is particularly preferable from an economical point of view.

The lipids may be extracted with organic solvent from the bacteria separated from the culture by conventional solid/liquid separative means such as centrifugation, filtration, etc. Alternatively, the lipids may be extracted with organic solvent from the bacteria-containing culture.

For more efficient extraction of lipids in this step, enzyme treatment with, for example, lysozyme, mechanical treatment with ultrasonication or by homogenizer etc., and chemical treatment with acids such as hydrochloric acid, sulfuric acid, etc. may be conducted prior to, or simultaneously with, extraction of lipids to decompose or disrupt at least a part of bacterial cell. If desired, the enzyme treatment, mechanical treatment and chemical treatment may be carried out simultaneously or successively.

The above extraction of lipids is carried out in a usual manner using solvent such as methanol, ethanol, butanol, acetone, hexane, diethylether, chloroform, etc., singly or as a mixed solvent.

According to the present invention, there can be produced lipids used widely as starting materials for surface active agents, food additives, and fatty acid in a wide variety of fields such as oil chemistry, petroleum chemistry, pharmaceuticals, agricultural chemicals, cosmetics and foods.

Further, the lipids obtained in the manner described above can be used as cosmetics suitable for hair, skin, etc. with the effects of hair growth promotion, moisturizing, cutaneous blood flow promotion, etc. The cosmetics may be in any of the forms which permit the lipids to demonstrate the effects, e.g. in the form of a preparation containing an extract obtained from the culture and bacteria in the manner described above and/or by the enzyme, mechanical, or chemical treatments as described above, as well as a preparation containing an extract further purified by various treatments as the active ingredient. If desired, the lipids may be purified in conventional procedures including recrystallization, column chromatography, distillation, etc.

The cosmetics of the present invention are prepared by incorporating lipids as the active ingredient usually in the range of 0.01 to 10% which is selected suitably depending on use, form, etc. of cosmetic.

The cosmetics of the present invention comprise other conventional ingredients selected suitably depending on use, type, form, etc., including base materials such as distilled water, alcohols, polyhydric alcohols, surface active agent, lipids, and polysaccharides, colorant, perfume, vitamins, amino acids, hormones, vasodilator drug, antiinflammatory agent, keratin-solubilizing agent, germicide, etc.

The cosmetics can be formed into liquid, powder, paste, etc. depending on use as products, e.g. hair growing agent, hair cream, hair tonic, hair lotion, shampoo, rinse, skin cream, etc.

According to the present invention, lipids can be produced stably without using any materials derived from natural animal or plant sources, and artificial lipids containing fatty acid residues with odd-numbered carbons can also be produced.

DESCRIPTION OF THE PREFERRED EMBODIMENTS

The present invention is described in more detail with reference to the following examples, which however are not intended to limit the scope of the present invention.

The lipids in a product can be easily identified by analysis of triglyceride, diglyceride, monoglyceride, phospholipids, etc., in thin layer chromatography. For example, each spot of triglyceride etc. can be visualized by spraying it with a solution of phosphomolybdic acid after development on a thin layer chromatography plate coated with silica gel in 0.25 mm thickness (e.g. silica gel 60 Art. 5721 available from Merck) with hexane:ether:acetic acid (80:20:1 v/v) as the developing solvent.

The fatty acid residues in lipids can be easily analyzed by gas chromatography following saponification of lipids with alkali, extraction of the released fatty acid with solvent such as hexane, and conventional methylesterification of the fatty acid. The analysis conditions for gas chromatography can be suitably selected depending on the fatty acid residue composition etc. in lipids. For example, methyl esters of $C_8$ to $C_{18}$ fatty acid can be analyzed using a column such as a capillary column (e.g. CPS-1 produced by QUADREX) (0.25 mm×25 m) with methyl cyanopropyl silicone as the liquid phase with an increasing temperature from 150° to 200° C. at a rate of 2° C./min. after keeping the column temperature at 150° C. for 15 min.

EXAMPLE 1

Fifty ml medium consisting of 1 g ammonium sulfate, 4 g dipotassium hydrogen phosphate, 2 g potassium dihydrogen phosphate, 0.5 g magnesium sulfate .7H$_2$O, 0.01 g iron (II) sulfate.7H$_2$O, 0.01 g manganese sulfate .nH$_2$O, 2 g yeast extract and 1000 ml distilled water was introduced into 500 ml Erlenmeyer flask and sterilized in an autoclave at 121° C. for 15 min., followed by addition of sterilized pentadecane in an amount of 50 ml relative to 1000 ml medium. *Mycobacterium sp.* KO-201 (FERM BP-5157) was inoculated onto it and cultured at 30° C. for 7 days under shaking. The bacteria were separated from the culture broth by centrifugation and extracted overnight with a mixed solvent of chloroform:methanol (2:1 v/v), followed by removal of the bacteria by centrifugation, removal of impurities by the Folch method, and removal of the solvent to give lipids in an amount of 7.9 g per liter of the culture. Analysis by thin layer chromatography indicated that the product is lipids containing triglyceride as the main component in addition to diglyceride, phospholipids, etc. The analysis of the fatty acid composition in the lipids indicated that the main component is pentadecanoic acid, i.e. a chain fatty acid with odd-numbered carbons.

EXAMPLE 2

The same medium was sterilized in the same manner as in Example 1, and octane (8 carbon atoms), nonane (9 carbon atoms), decane (10 carbon atoms), tridecane (13 carbon atoms), tetradecane (14 carbon atoms), heptadecane (17 carbon atoms) or octadecane (18 carbon atoms) was added to the medium as the aliphatic hydrocarbons. *Mycobacterium sp.* KO-201 (FERM BP-5157) was inoculated onto it and cultured at 30° C. for 7 days under shaking to give lipids in each culture. The results are shown in Table 2.

TABLE 2

| aliphatic hydrocarbons | | production of lipids |
|---|---|---|
| octane | 8 carbon atoms | 0.1 g/L |
| nonane | 9 carbon atoms | 0.4 g/L |
| decane | 10 carbon atoms | 0.1 g/L |
| tridecane | 13 carbon atoms | 0.6 g/L |
| tetradecane | 14 carbon atoms | 7.3 g/L |
| heptadecane | 17 carbon atoms | 8.0 g/L |
| octadecane | 18 carbon atoms | 2.4 g/L |

EXAMPLE 3

As the aliphatic hydrocarbons, pentadecane was added in an amount of 50 ml every 1000 ml medium containing 1 g/L ammonium sulfate, 2 g/L potassium dihydrogen phosphate, 4 g/L dipotassium hydrogen phosphate, 0.5 g/L magnesium sulfate .7H$_2$O, 0.01 g/L iron (II) sulfate.7H$_2$O, 0.01 g/L manganese sulfate .nH$_2$O, 1 g/L yeast extract and 1 g/L peptone. *Corynebacterium fujiokense* ATCC 21496, *Rhodococcus rhodochrous* ATCC 13808, *Arthrobacter paraffineus* ATCC 15591 or *Brevibacterium ketoglutamicum* ATCC 15588 was inoculated onto the medium and cultured at 30 ° C. for 7 days under shaking in the same manner as in Example 1. The production of lipids was observed in each culture. The results are shown in Table 3.

TABLE 3

| bacteria | production of lipids |
|---|---|
| *Corynebacterium fujiokense* ATCC 21496 | 4.1 g/L |
| *Rhodococcus rhodochrous* ATCC 13808 | 6.0 g/L |
| *Arthrobacter paraffineus* ATCC 15591 | 4.4 g/L |
| *Brevibacterium ketoglutamicum* ATCC 15588 | 9.7 g/L |

EXAMPLE 4

2.5 L medium consisting of 3 g ammonium sulfate, 4 g dipotassium hydrogen phosphate, 2 g potassium dihydrogen phosphate, 0.5 g magnesium sulfate .7H$_2$O, 0.01 g calcium chloride.2H$_2$O, 0.01 g iron (II) sulfate.7H$_2$O, 0.01 g manganese sulfate .nH$_2$O, 0.01 g zinc sulfate.7H$_2$O, 1 g yeast extract, 50 ml pentadecane and 1000 ml distilled water was introduced into 5 L fermentor and sterilized in an autoclave at 121° C. for 20 min. *Agrobacterium sp.* KO-202 or *Rhizobium sp.* KO-203 was inoculated onto the medium and cultured for 7 days at 30° C., pH 5.5. The bacteria were separated from the culture by centrifugation, followed by extraction and removal of the solvent in the same manner as in Example 1 to give the amounts of lipids shown in Table 4.

TABLE 4

|  | *Agrobacterium* sp. KO-202 | *Rhizobium* sp. KO-203 |
| --- | --- | --- |
| production of lipids | 9.6 g/L | 7.0 g/L |

EXAMPLE 5

100 ml pentadecane was added as the aliphatic hydrocarbons to medium (pH 6.9) consisting of 4.5 g ammonium sulfate, 4.0 g dipotassium hydrogen phosphate, 2.0 g potassium dihydrogen phosphate, 0.5 g magnesium sulfate $.7H_2O$, 0.01 g iron (II) sulfate.$7H_2O$, 0.01 g manganese sulfate .$nH_2O$, 0.01 g calcium chloride.$2H_2O$, 1.0 g yeast extract and 1000 ml distilled water and the medium was sterilized in an autoclave at 121° C. for 15 min. After cooling, *Mycobacterium sp.* KO-201 (FERM BP-5157), *Agrobacterium sp.* KO-202 (FERM BP-5158), *Rhizobium sp.* KO-203 (FERM BP-5159), *Arthrobacter paraffineus* ATCC 15591 or *Brevibacterium ketoglutamicum* ATCC 15588 was inoculated respectively onto the above medium and cultured aerobically at 30° C. for 7 days under shaking.

After culture was finished, the bacteria were separated from each culture broth by centrifugation and extracted with a mixed solvent of chloroform:methanol (2:1 V/V), followed by removal of impurities by the Folch method and removal of the solvent to give lipids containing glycerides of fatty acid as the main component. These lipids were dissolved at a concentration 1 W/V (g/100 ml) % in ethanol and evaluated in the following tests.

Male New Zealand white rabbits (clean, weighting 2.5 to 3.0 kg) at telogen stage each group consisting of 5 animals were used after the hairs on the back were clipped to examine the effects of the sample on hair restoration, moisturizing of skin moisture, increase of cutaneous blood flow.

To examine hair restoration, 0.2 ml sample was applied once per day onto the bared back for 6 weeks, and the restoration of hairs was evaluated according to the criteria in Table 5 showing the number days by which hair restoration was promoted as compared with the control where only ethanol was applied.

To examine moisturizing of skin moisture and increase of cutaneous blood flow, 0.2 ml sample was applied 4 times per day onto the bared back for 2 weeks. Before the first application and 2 hours after the final application of the sample, the bared back was washed quickly with soap for removal of fats on the skin, and 1 hour thereafter, the content of water in the skin was determined with an apparatus of measuring skin moisture, and the volume of cutaneous blood flow was determined with a laser Doppler flowmeter. The criteria used for evaluation are shown in Table 5 where the original value before application of the sample is assumed to be 100 %.

The results indicated that the sample containing lipids according to the present invention has effects on hair restoration, moisturizing of skin moisture and increase in cutaneous blood flow. The results are shown in Table 6.

TABLE 5

| hair restoration | | moisturizing of skin | | cutaneous blood flow | |
| --- | --- | --- | --- | --- | --- |
| promotion days | result | increase | result | increase | result |
| 10 or more days | ++ | 111% or more | ++ | 121% or more | + |
| 3 to 9 days | + | 101–110% | + | 111–120% | + |
| 2 or less days | – | 100% or less | – | 110% or less | – |

TABLE 6

| bacteria | | Mycobacterium sp. KO-201 | Agrobacterium sp. KO-202 | Rhizobium sp. KO-203 | Arthrobacter paraffineus ATCC 15591 | Brevibacterium ketoglutamicum ATCC 15588 |
| --- | --- | --- | --- | --- | --- | --- |
| test items | hair restoration effect | + | + | + | + | + |
|  | moisturizing of skin | + |  |  |  |  |
|  | cutaneous blood flow | ++ |  |  |  |  |

EXAMPLE 6

A hair growing agent of the following formulation was prepared.

| ethyl alcohol | 50.0 weight-% |
| --- | --- |
| lipids obtained in Example 1 | 1.0 weight-% |
| polyoxyethylene (9 moles) lauryl ether | 2.0 weight-% |
| perfume | suitable amount |
| distilled water | remainder |

EXAMPLE 7

A skin lotion of the following formulation was prepared.

| oleyl alcohol | 4.0 weight-% |
| --- | --- |
| glycerin | 2.0 weight-% |
| lipids obtained in Example 1 | 2.0 weight-% |
| polyethylene glycol (40 moles) stearate | 4.0 weight-% |
| 1 weight-% aqueous carboxymethylcellulose | 20.0 weight-% |
| sodium salicylate | 0.1 weight-% |
| perfume | suitable amount |
| distilled water | remainder |

EXAMPLE 8

A skin cream of the following formulation was prepared.

| | |
|---|---|
| stearic acid | 2.0 weight-% |
| stearyl alcohol | 5.0 weight-% |
| liquid paraffin | 10.0 weight-% |
| lipids obtained in Example 1 | 4.0 weight-% |
| sorbitan monostearate | 2.0 weight-% |
| polyoxyethylene (20 moles)sorbitan monostearate | 3.0 weight-% |
| ethyl p-oxybenzoate | 0.1 weight-% |
| perfume | suitable amount |
| distilled water | remainder |

What is claimed is:

1. A process for producing lipids comprising glycerides as the main component, which comprises culturing a bacterium selected from the group consisting of Mycobacterium sp. KO-201 (FERM BP-5157), Agrobacterium sp. KO-202 (FERM BP-5158), and Rhizobium sp. KO-203 (FERM BP-5159) in medium containing aliphatic hydrocarbons until lipids are accumulated in the bacterium and then recovering the lipids therefrom.

2. A process according to claim 1, wherein the bacterium is *Mycobacterium sp.* KO-201 (FERM BP-5157).

3. A process according to claim 1, wherein the bacterium is *Agrobacterium sp.* KO-202 (FERM BP-5158).

4. A process according to claim 1, wherein the bacteria is *Rhizobium sp.* KO-203 (FERM BP-5159).

5. A process according to claim 1, wherein fatty acid residues with odd-numbered carbons are contained in fatty acid residues in the lipids.

6. A process according to claim 1, wherein the aliphatic hydrocarbons contain aliphatic hydrocarbons with odd-numbered carbons.

7. A process according to claim 1, wherein the aliphatic hydrocarbons are aliphatic hydrocarbons with 8 to 20 carbon atoms.

8. A process according to claim 1, wherein the aliphatic hydrocarbons are straight aliphatic hydrocarbons with 8 to 20 carbon atoms.

9. A process according to claim 1, wherein the medium pH is in the range of 4 to 8.

10. A process according to claim 1, wherein the culture temperature is in the range of 20 to 35° C.

11. A process according to claim 1, wherein the recovered lipids comprise triglycerides as the main component.

12. A process according to claim 11, wherein the recovered lipids further comprise diglycerides.

13. A process according to claim 12, wherein the recovered lipids further comprise monoglycerides.

14. A process according to claim 13, wherein the recovered lipids further comprise phospholipids.

* * * * *